(12) United States Patent
Faig et al.

(10) Patent No.: US 10,864,151 B1
(45) Date of Patent: Dec. 15, 2020

(54) EMULSIFIER-FREE HYDROXY ACID GEL CREAM COMPOSITION

(71) Applicant: L'OREAL, Paris (FR)

(72) Inventors: Jonathan James Faig, Sayersville, NJ (US); David Chan, Edison, NJ (US); Maximillian Baria, River Edge, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/427,085

(22) Filed: May 30, 2019

(51) Int. Cl.
| | | |
|---|---|---|
| *A61K 8/365* | (2006.01) |
| *A61K 8/04* | (2006.01) |
| *A61K 8/92* | (2006.01) |
| *A61Q 19/00* | (2006.01) |
| *A61K 8/81* | (2006.01) |

(52) U.S. Cl.
CPC ............. *A61K 8/365* (2013.01); *A61K 8/042* (2013.01); *A61K 8/8158* (2013.01); *A61K 8/92* (2013.01); *A61Q 19/00* (2013.01); *A61K 2800/33* (2013.01); *A61K 2800/48* (2013.01)

(58) Field of Classification Search
CPC ........ A61K 8/365; A61K 8/042; A61K 8/092; A61K 19/00; A61K 8/8158; A61K 2800/48; A61K 2800/33
See application file for complete search history.

(56) References Cited

U.S. PATENT DOCUMENTS

| | | |
|---|---|---|
| 6,986,895 B2 | 1/2006 | Suares et al. |
| 2003/0124158 A1 | 7/2003 | Heidenfelder et al. |
| 2013/0302452 A1 | 11/2013 | Brieva et al. |

FOREIGN PATENT DOCUMENTS

| | | | |
|---|---|---|---|
| CA | 2935367 | * | 1/2017 |
| KR | 20120070192 A | | 6/2012 |
| WO | 03022236 A1 | | 3/2003 |

OTHER PUBLICATIONS

Mintel, Iridescent Tented Cream Gel, The Lierac Sunific Autobronzant, Mintel, www.gnpd.com.
International Search Report for PCT/US2020/033200, dated Jul. 13, 2020.

\* cited by examiner

*Primary Examiner* — Shirley V Gembeh
(74) *Attorney, Agent, or Firm* — McNees Wallace & Nurick LLC

(57) ABSTRACT

An emulsifier-free composition includes in a water phase a hydroxy acid system that includes alpha hydroxy, a blend of low pH, high electrolyte compatible thickeners and in an oily phase one or a combination of emollient oils. The composition has a pH in the range from about 1 to about 5.0 and is essentially free of emulsifiers and comprises a gel cream architecture.

20 Claims, No Drawings

EMULSIFIER-FREE HYDROXY ACID GEL CREAM COMPOSITION

FIELD

The present disclosure is directed to skin care compositions that provide hydroxy acid at a low pH that is below 5.0 having a gel cream texture that shear thins to a serum-like fluid in the absence of emulsifier.

BACKGROUND

Various cosmetic products are formulated with components that require a relatively low pH and high salt content. These include products that contain hydroxy acids, such as alpha-hydroxy and beta-hydroxy acids, of which glycolic acid and salicylic acid, respectively, are examples. Such products provide benefits that include softer, smoother and tighter skin, and an overall even complexion with reduced facial lines. But due to the low pH and higher salt content which are necessary to incorporate glycolic acid and other hydroxy acids at useful concentrations, these compositions prove challenging to thicken. Typically, these compositions are thin and watery, and can be displeasing to consumers who prefer products with a thick, rich and creamy texture that is fresh and non-greasy when applied to the skin. Some solutions for improving the texture of such products include reduction of the amount of hydroxy acid and addition of emulsifiers which enable the use of thickeners and emollients to provide a more desirable sensorial experience. Of course, reduced amounts of the hydroxy acids can adversely impact efficacy of the product in favor of a better sensorial experience. And inclusion of emulsifiers can result in a tacky, sticky effect, and in some instances create a haze or whitening to the skin upon application. Currently, there are no emulsifier-free glycolic acid creams.

In view of the foregoing, there is a need in the art for a cosmetic composition that tolerates low pH and high salt content without sacrificing desirable sensorial properties. The instant disclosure provides a composition that tolerates a broad range of hydroxy acid content without emulsifiers in a gel cream architecture characterized as having a pressed serum-like cream texture that has an initial rigid pick-up and shear thins to a fluid, serum-like texture.

SUMMARY

The disclosure provides, in various embodiments, an emulsifier-free composition that includes in a water phase a hydroxy acid system that includes alpha hydroxy, a blend of low pH, high electrolyte compatible thickeners and in an oily phase one or a combination of emollient oils. The composition has a pH in the range from about 1 to about 5.0 and is essentially free of emulsifiers and comprises a gel cream architecture.

A cosmetic composition that includes:
a) a water phase, comprising;
  i. a hydroxy acid system comprising alpha hydroxy acid;
  ii. a primary low pH, high electrolyte compatible thickener comprising Hydroxyethyl Acrylate/Sodium Acrrloyldimethyl Taurate Copolymer;
  iii. at least one secondary low pH, high electrolyte compatible thickener; and
  iv. water, and
b) an oil phase, comprising:
  i. one or a combination of emollient oils, butters and waxes.

In accordance with the various embodiments, the composition has a pH in the range from about 1 to about 5.0 and is essentially free of emulsifiers, and wherein the composition comprises a gel cream architecture.

In some embodiments, the composition is essentially free or devoid of emulsifiers selected from surfactants with a C10-C20 fatty alcohol or acid hydrophobe condensed with from about 2 to about 100 moles of ethylene oxide or propylene oxide per mole of hydrophobe; C2-C10 alkyl phenols condensed with from 2 to 20 moles of alkylene oxide; mono- and di-fatty acid esters of ethylene glycol; fatty acid monoglyceride; sorbitan; mono- and di-C8-C20 fatty acids; polyoxyethylene sorbitan; alkyl polyglycosides and saccharide fatty amides (e.g. methyl gluconamides); alkyl ether sulfate and sulfonates; alkyl sulfates and sulfonates; alkylbenzene sulfonates; alkyl and dialkyl sulfosuccinates; C8-C20 acyl isethionates; C8-C20 alkyl ether phosphates; alkylethercarboxylate. Some specific emulsifiers that are lacking from the composition include PEG-100 Stearate; PEG-20 Stearate and other esters of Poly(Ethylene Glycol); Sucrose Stearate and other emulsifiers based on sugar esters; Glyceryl Stearate and other glycerol esters; Disodium Ethylene Dicocamide PEG-15 Disulfate; Sodium Steroyl Glutamate and other fatty amides; Steareth-100 and other fatty ethers; Acrylates/C10-30 Alkyl Acrylate Crosspolymer and combinations of these.

In some embodiments, the hydroxy acid system includes a combination of hydroxy acids selected from two or more alpha hydroxy acids, at least one alpha hydroxy acid and at least one beta hydroxy acid, and two or more alpha hydroxy acids and at least one beta hydroxy acid. In some particular embodiments, the hydroxy acid system includes at least one of glycolic acid, lactic acid and citric acid and a beta hydroxy acid includes salicylic acid or a derivative thereof.

In some embodiments, the at least one secondary thickener includes one or more of Sodium Acryloyldimethyltaurate/VP Crosspolymer, Sodium Acryloyldimethyltaurate/VP Copolymer, Polyacrylamide (and) C13-14 Isoparaffin (and) Laureth-7, Carbomer, Acrylamide/Sodium Acryloyldimethyltaurate Copolymer (and) Isohexadecane (and) Polysorbate 80. In some particular embodiments, the at least one secondary thickener includes (a) one or both of Sodium Acryloyldimethyltaurate/VP Crosspolymer and Carbomer, and (b) one of Polyacrylamide (and) C13-14 Isoparaffin (and) Laureth-7 and Acrylamide/Sodium Acryloyldimethyltaurate Copolymer (and) Isohexadecane (and) Polysorbate 80.

In some embodiments, the one or a combination of emollients includes one or more of a fatty alcohol, a fatty acid ester, a alkyl glucoside, a silicone oil, and combinations of these. In some particular embodiments, the one or a combination of emollients includes octyldodecanol, diisopropyl adipate, isononyl isononanoate, limnanthes alba (meadowfoam) seed oil, dicaprylyl carbonate, squalane, dimethicone, and behenyl alcohol, and combinations of these.

In accordance with some embodiments, the hydroxy acid system is present from about 6% to more than about 20% by weight based on the weight of the composition.

In accordance with some embodiments, the primary thickener is present from about 0.5% to about 5% by weight based on the weight of the composition.

In accordance with some embodiments, each of the at least one secondary thickener is present from about 0.5% to about 8% by weight based on the weight of the composition.

In some particular embodiments, the primary low pH, high electrolyte compatible thickener is present from about 0.625% to about 2.5%, and each of the at least one secondary low pH, high electrolyte compatible thickener is present from about 0.5% to about 2%, each present by weight based on the total weight of the composition.

In some particular embodiments, the one or a combination of emollient oils is present from about 5% to more than about 20% by weight based on the weight of the composition.

In accordance with some embodiments, water is present from about 55% to about 80% by weight based on the weight of the composition.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

These and other aspects of the invention are set out in the appended claims and described in greater detail in the detailed description of the invention.

DETAILED DESCRIPTION

"Keratinous substrate" and "keratinous tissue" each includes but is not limited to skin, hair, and nails.

"Emulsifier Free" means compositions that lack or are essentially free of an emulsifier. Some specific but non-limiting examples of emulsifiers that are lacking from the composition includes surfactants with a C10-C20 fatty alcohol or acid hydrophobe condensed with from about 2 to about 100 moles of ethylene oxide or propylene oxide per mole of hydrophobe; C2-C10 alkyl phenols condensed with from 2 to 20 moles of alkylene oxide; mono- and di-fatty acid esters of ethylene glycol; fatty acid monoglyceride; sorbitan; mono- and di-C8-C20 fatty acids; polyoxyethylene sorbitan; alkyl polyglycosides and saccharide fatty amides (e.g. methyl gluconamides); alkyl ether sulfate and sulfonates; alkyl sulfates and sulfonates; alkylbenzene sulfonates; alkyl and dialkyl sulfosuccinates; C8-C20 acyl isethionates; C8-C20 alkyl ether phosphates; alkylethercarboxylate. Some specific emulsifiers that are lacking from the composition include PEG-100 Stearate; PEG-20 Stearate and other esters of Poly(Ethylene Glycol); Sucrose Stearate and other emulsifiers based on sugar esters; Glyceryl Stearate and other glycerol esters; Disodium Ethylene Dicocamide PEG-15 Disulfate; Sodium Steroyl Glutamate and other fatty amides; Steareth-100 and other fatty ethers; Acrylates/C10-30 Alkyl Acrylate Crosspolymer and similar polymeric emulsifiers.

The term "gel cream architecture" as used in the context of a cosmetic composition according to the disclosure refers to a composition that is characterized as having an initial rigid pick-up and shear thins to a fluid, serum-like texture that is semi-translucent to translucent and light and non-sticky on application.

The disclosure provides, in various embodiments, an emulsifier-free composition that includes in a water phase a hydroxy acid system that includes alpha hydroxy, a blend of low pH, high electrolyte compatible thickeners and in an oily phase one or a combination of emollient oils. The composition has a pH in the range from about 1 to about 5.0 and is essentially free of emulsifiers and comprises a gel cream architecture.

Prior art compositions that have a low pH and high salt content, such as hydroxy acid-containing compositions typically employ emulsifiers together with thickeners to achieve a desirable consistency. Such compositions suffer from employing limited amounts of hydroxy acids in order to achieve solubility of the acids and maintain textural and storage stability properties, thus diminishing the potential active benefits of the hydroxy acids. Inclusion of emulsifiers, such as emulsifying surfactants, can be associated with tackiness, unwanted whitening upon application, and with skin drying and irritation and overall loss of skin hydration.

According to the disclosure, the inventive compositions overcome the shortcomings of the prior art and provide benefits that include the unexpected ability to incorporate high amounts of hydroxy acids in the absence of emulsifiers, particularly emulsifying surfactants, to provide a suspension of an emollient oily phase with the consumer preferred features of a gel cream. The composition includes in various embodiments hydroxy acids, particularly alpha hydroxy acids, with a blend of low pH, high electrolyte compatible thickeners in the water phase to provide a thickened water phase that supports a suspension of emollient oils.

Thus, compositions in accordance with the disclosure are free of emulsifiers, particularly emulsifying surfactants, are formulated to provide clear and aesthetically pleasing application to the skin in a gel cream architecture.

Aqueous Phase

In accordance with the disclosure, the aqueous phase is present in the composition and includes water present in the range from about 55% to about 80%. In some embodiments, the aqueous phase also includes one or more hydrating agent present from about 5% to about 25% by weight, all based on the total weight of the composition.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the composition is not limited but is generally between 1 and 5.0, and in some embodiments, is one of between 2 and 5, or between 3 and 4. Generally, the pH can be adjusted to the desired value by addition of a base or an acid (organic or inorganic). In view of the inclusion of hydroxy acids in the compositions hereof, the pH is typically adjusted using a base, which in some examples is sodium hydroxide.

Hydroxy Acids

In accordance with the various embodiments, the composition includes one or a combination of hydroxy acids selected from alpha hydroxy acids and beta hydroxy acids. In some particular embodiments, the compositions include at least one or more alpha hydroxy acids. The total amount of hydroxy acids includes in some embodiments up to and not more than about 6% hydroxy acids. In other embodiments, the compositions include at least about 20% and up to about 30% hydroxy acid. In yet other embodiments, the compositions include from about 6% to about 20% hydroxy acid. In some embodiments, the compositions include from about 6% to about 20% of one or a combination of alpha hydroxy acids. In some embodiments, the compositions include from about 6% to about 20% of one or a combination of alpha hydroxy acids, and up to about 2% of beta hydroxy acid.

The term "alpha-hydroxy acid" is understood to mean, according to the present invention, a carboxylic acid having at least one hydroxyl functional group occupying an alpha-position on said acid (carbon adjacent to a carboxylic acid functional group). A beta-hydroxy acid is closely related to an alpha-hydroxy acid except the carboxylic and hydroxyl functional groups are separated by two carbon atoms. A hydroxy acid can be present in the final composition in the form of the free acid and/or in the form of one of its associated salts (salts with an organic base or an alkali metal, in particular), especially according to the final pH imposed on the composition.

The alpha hydroxy acid present in the cosmetic composition, according to the disclosure, includes, but is not limited to, one or more of glycolic acid, citric acid, lactic acid, methyllactic acid, glucuronic acid, pyruvic acid, 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytetradecanoic acid, 2-hydroxyhexadecanoic acid, 2-hydroxyoctadecanoic acid, 2-hydroxytetracosanoic acid, 2-hydroxyeicosanoic acid, mandelic acid, phenyllactic acid, gluconic acid, galacturonic acid, aleuritic acid, ribonic acid, tartronic acid, tartaric acid, malic acid, fumaric acid, their salts and their mixtures. It is also possible to use mixtures of these various acids.

In some embodiments, the composition includes alpha hydroxy acids comprising glycolic acid and one or more of citric acid and lactic acid. When combined, the more than one alpha hydroxy acids may be present in the same or in different amounts.

The beta hydroxy acid, when present in the cosmetic composition according to the disclosure, includes, but is not limited to, one or more of salicylic acid and derivatives thereof (including 5-n-octanoylsalicylic acid, salicylate, sodium salicylate, and willow extract), beta hydroxybutanoic acid, tropic acid, and trethocanic acid.

In some embodiments, the composition includes a beta hydroxy acid comprising salicylic acid.

In accordance with the various embodiments, the amount of hydroxy acid present in the compositions can range from about 3% to about 25%, or from about 5% to about 20%, or from about 7% to about 15% or any suitable combination, sub-combination, range, or sub-range thereof by weight, based on the weight of the composition. One of ordinary skill in the art, however, will appreciate that other ranges are within the scope of the invention.

In accordance with the various embodiments, the amount of alpha-hydroxy acid present in the compositions can range from about 3% to about 25%, or from about 5% to about 20%, or from about 7% to about 15% or any suitable combination, sub-combination, range, or sub-range thereof by weight, based on the weight of the composition. One of ordinary skill in the art, however, will appreciate that other ranges are within the scope of the invention.

In accordance with the various embodiments, the amount of beta-hydroxy acid present in the compositions can range from about 0.1% to about 10%, or from about 0.2% to about 5%, or from about 0.2% to about 2% or any suitable combination, sub-combination, range, or sub-range thereof by weight, based on the weight of the composition. One of ordinary skill in the art, however, will appreciate that other ranges are within the scope of the invention.

Thus, any one of or a combination of hydroxy acids may be present, by weight, based on the total weight of the composition, each present from about 0.1, 0.2, 0.3, 0.4, 0.5, 0.6, 0.7, 0.8, 0.9, 1.0, 2, 3, 4, 5, 6, 7, 8, 9, to about 10 weight percent, including increments and ranges therein and therebetween.

Thickener

In accordance with the various embodiments, the composition includes a blend of thickeners that comprise low pH, high electrolyte compatible thickeners. In the various embodiments, the total amount of each thickener is from about 0.1% to about 5.0% by weight, based on the total weight of the composition. In the various embodiments, the total amount of the blend of thickeners in the compositions is from about 2% to about 8% by weight, based on the total weight of the composition.

In some embodiments, the blend of low pH, high electrolyte compatible thickeners comprises a primary thickener comprising Hydroxyethyl Acrylate/Sodium Acrrloyldimethyl Taurate Copolymer, and one or more of secondary thickeners selected from Sodium Acryloyldimethyltaurate/VP Crosspolymer, Sodium Acryloyldimethyltaurate/VP Copolymer, Polyacrylamide (and) C13-14 Isoparaffin (and) Laureth-7, Carbomer, Acrylamide/Sodium Acryloyldimethyltaurate Copolymer (and) Isohexadecane (and) Polysorbate 80.

In some embodiments, the at blend of thickeners comprises (a) one or both of Sodium Acryloyldimethyltaurate/VP Crosspolymer and Carbomer, and (b) one of Polyacrylamide (and) C13-14 Isoparaffin (and) Laureth-7 and Acrylamide/Sodium Acryloyldimethyltaurate Copolymer (and) Isohexadecane (and) Polysorbate 80.

In some embodiments, the at blend of thickeners comprises (a) both of Sodium Acryloyldimethyltaurate/VP Crosspolymer and Carbomer, and (b) one of Polyacrylamide (and) C13-14 Isoparaffin (and) Laureth-7 and Acrylamide/Sodium Acryloyldimethyltaurate Copolymer (and) Isohexadecane (and) Polysorbate 80.

In some embodiments, the at blend of thickeners comprises (a) each of secondary thickeners Sodium Acryloyldimethyltaurate/VP Crosspolymer, Polyacrylamide (and) C13-14 Isoparaffin (and) Laureth-7, and Carbomer, or (b) each of secondary thickeners Sodium Acryloyldimethyltaurate/VP Copolymer, Polyacrylamide (and) C13-14 Isoparaffin (and) Laureth-7, Carbomer, or (c) each of secondary thickeners Sodium Acryloyldimethyltaurate/VP Crosspolymer, Carbomer, and Acrylamide/Sodium Acryloyldimethyltaurate Copolymer (and) Isohexadecane (and) Polysorbate 80, or (d) each of secondary thickeners Sodium Acryloyldimethyltaurate/VP Copolymer, Carbomer, and Acrylamide/Sodium Acryloyldimethyltaurate Copolymer (and) Isohexadecane (and) Polysorbate 80.

In accordance with the various embodiments, the amount of the primary thickener is present from about 0.1% to about 5%, or from about 0.2% to about 4%, or from about 0.6% to about 3%, or from about 1% to about 2%, and the amount of an individual secondary thickener is present from about 0.1% to about 8%, or from about 0.2% to about 4%, or from about 0.5% to about 3%, or from about 1% to about 2% based on the total weight of the composition.

In accordance with some embodiments, the composition comprises combinations of Hydroxyethyl Acrylate/Sodium Acrrloyldimethyl Taurate Copolymer present in the range from about 0.625% to about 2.5%; Sodium Acryloyldimethyltaurate/VP Crosspolymer present in the range from about 0.625% to about 2.5; Sodium Acryloyldimethyltaurate/VP Copolymer present in the range from about 0.625% to about 2.5%; Polyacrylamide (and) C13-14 ISOPARAFFIN (and) Laureth-7 present in the range from about 0% to about 5%; Carbomer present in the range from about 0% to about 1%; Acrylamide/Sodium Acryloyldimethyltaurate Copolymer (and) Isohexadecane (and) Polysorbate 80 present in the range from about 0% to about 2.5%.

In accordance with the various embodiments, the total amount of thickeners in the composition is present from about 2.0% to about 8.0%, or from about 2.0% to about 7.5%, or from about 2.0% to about 7.0%, or from about 2.1% to about 6.5%, or from about 2.125% to about 6.125%, or from about 3% to about 5% based on the total weight of the composition.

Thus, the amount of a thickener present in the composition is present by weight, based on the total weight of the composition, from about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5 to about 5.0 percent, including increments and ranges therein and there between. And in combination, total amount of thickeners in the composition are present by weight, based on the total weight of the composition, from about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, to about 8 percent, including increments and ranges therein and there between.

Hydrating Agent

In accordance with the disclosure, one or more hydrating agents may be present in the composition. The hydrating agent present in the cosmetic composition, according to the disclosure, includes, but is not limited to, one or more of polyols, including, for example, glycerin, glycerol, glycols, such as caprylyl glycol, butylene glycol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers such as monopropylene, dipropylene and tripropylene glycol alkyl(C1-C4)ethers, squalane, triacetin, sugars, such as glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some embodiments, the composition includes a hydrating agent selected from one or a combination of glycerin and butylene glycol. In some particular embodiments, the composition comprises about 10% glycerin.

In accordance with the various embodiments, the amount of hydrating agent present in the compositions can range from about 3% to about 25%, or from about 5% to about 20%, or from about 7% to about 15% or any suitable combination, sub-combination, range, or sub-range thereof by weight, based on the weight of the composition. One of ordinary skill in the art, however, will appreciate that other ranges are within the scope of the invention.

Thus, any one of or a combination of hydrating agent may be present, by weight, based on the total weight of the composition, is from about 3, 4, 5, 6, 7, 8, 9, 10, 11, 12, 13, 14, 15, 16, 17, 18, 19, 20, 21, 22, 23, 24, to about 25 weight percent, including increments and ranges therein and there between.

Oily Phase

Emollients

The oily phase present in the composition according to the disclosure includes, in some embodiments, at least one emollient oil. In accordance with the various embodiments, nonlimiting examples of emollient oils include one or more of a fatty alcohol, a fatty acid ester, a silicone oil, and combinations of these.

In accordance with some embodiments, the composition comprises one or more emollient oils selected from octyldodecanol, diisopropyl adipate, isononyl isononanoate, limnanthes alba (meadowfoam) seed oil, dicaprylyl carbonate, squalane, dimethicone, and behenyl alcohol.

In some representative embodiments, the composition comprises a combination of at least two of emollients selected from octyldodecanol, diisopropyl adipate, isononyl isononanoate, limnanthes alba (meadowfoam) seed oil, dicaprylyl carbonate, squalane, dimethicone, and behenyl alcohol.

In accordance with the various embodiments, the amount of an emollient oil present in the compositions can range from about 0.5% to about 6%, or from about 0.5% to about 3%, or from about 1% to about 1.5%, or any suitable combination, sub-combination, range, or sub-range thereof by weight, based on the weight of the composition. One of ordinary skill in the art, however, will appreciate that other ranges are within the scope of the invention.

In accordance with some embodiments, the composition comprises one or more of octyldodecanol present at about 0.5%, diisopropyl adipate present at about 1.5%, isononyl isononanoate present at about 6%, limnanthes alba (meadowfoam) seed oil present at about 3%, dicaprylyl carbonate present at about 3%, squalane present at about 3%, dimethicone is present at about 0.5%, and behenyl alcohol present at about 1%.

In accordance with the various embodiments, the amount of combined emollient oil present in the compositions can range from about 5% to about 20%, or from about 5% to about 15%, or from about 5% to about 10%, or any suitable combination, sub-combination, range, or sub-range thereof by weight, based on the weight of the composition. One of ordinary skill in the art, however, will appreciate that other ranges are within the scope of the invention.

Thus, an emollient oil in the composition may be present by weight, based on the total weight of the composition, from about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.0, 5.1, 5.2, 5.3, 5.4, 5.5, 5.6, 5.7, 5.8, 5.9, to about 6.0 percent, including increments and ranges therein and there between. And in combination, emollient oils in the composition may be present by weight, based on the total weight of the composition, from about 1, 2, 3, 4, 5, 6, 7, 8, 9, 10, 11, 12, 13, 14, 15, 16, 17, 18, 19, to about 20 percent, including increments and ranges therein and there between.

Optional Additives

The compositions can also comprise, in one or both of the water and the oily phases, as appropriate, at least one additive used in the cosmetics field which does not affect the properties of the compositions according to the invention, such as fragrances, pearlescent agents, silica, preservatives, proteins, protein hydrolysates, vitamins, panthenol, silicones, odor absorbers and coloring materials; anti-microbial components, including, but not limited to, capryloyl glycine and sodium salicylate; essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang; fruit extracts, for example Pyrus Malus (Apple) Fruit Extract, and Aloe Barbadensis Leaf Juice Powder; citric acid, sodium chloride; neutralizing or pH-adjusting agents (e.g., triethylamine (TEA) and sodium hydroxide), and combinations thereof. Additives may also include UV actives, and SPF boosters which may include light refracting bodies and materials that include a styrene-acrylate copolymer composition. Although the optional active additives are given as examples, it will be appreciated that other optional components compatible with cosmetic applications known in the art may be used.

In accordance with the various embodiments, the amount of one or more additives, alone or in combination, present in the composition can be present in the composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the composition.

Thus, any one or a combination of additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

EXAMPLES

Example 1: Evaluating Thickened Compositions that Incorporate Hydroxy Acids without Emulsifiers A series of thickeners, in particular low pH, high electrolyte compatible thickeners, were screened for their capacity to thicken an aqueous system with 10% glycolic acid that was adjusted with sodium hydroxide to a pH of 4. The thickeners included raw material ingredients (RMI) as 1-6 listed below in Table 1, in addition to other thickeners selected from polyacrylate crosspolymer-6, ammonium polyacryloyldimethyl taurate, Aristoflex HMS, and Pemulen EZ4U. Upon confirming that compositions with high hydroxy acid could be formulated in the absence of emulsifiers, a subset of thickeners were selected for further evaluation to provide desirable emulsifier-free gel cream compositions with even greater hydroxy acid content.

Example 2: Formulating Compositions that Accommodate High Glycolic Acid at Low pH in the Absence of Emulsifiers Following the tests conducted under Example 1, thickeners 1, 2, 4 and 5 were further employed to formulate compositions having a gel cream architecture.

TABLE 1

| RMI REF # | RMI CHEMICAL NAME | RMI COMMERCIAL EXAMPLE |
|---|---|---|
| #1 | Hydroxyethyl Acrylate/Sodium Acrrloyldimethyl Taurate Copolymer (EMT) | SEPINOV WMR (SEPPIC) |
| #2 | Sodium Acryloyldimethyltaurate/ VP Crosspolymer | ARISTOFLEX AVS (CLARIANT CORPORATION) |
| #3 | Sodium Acryloyldimethyltaurate/ VP Copolymer | ARISTOFLEX AVC (CLARIANT CORPORATION) |
| #4 | Polyacrylamide (and) C13-14 Isoparaffin (and) Laureth-7 | SEIPIGEL (SEPPIC) |
| #5 | Carbomer | CARBOPOL ULTREZ 30 POLYMER (LUBRIZOL) |
| #6 | Acrylamide/Sodium Acryloyldimethyltaurate Copolymer (and) Isohexadecane (and) Polysorbate 80 | SIMULGEL (SEPPIC) |
| #7 | OIL BLEND: Behenyl Alcohol, Isononyl Isononanoate, Dicapryl Carbonate | |
| #8 | AHA: Glycolic Acid | |

A series of thickeners, in particular low pH, high electrolyte compatible thickeners, were screened for their capacity to thicken an aqueous system with 10% emollient oil and 14.4% glycolic acid that was adjusted with sodium hydroxide to a pH of 4. The design of experiment revealed that the use of Hydroxyethyl Acrylate/Sodium Acryloyldimethyltaurate Copolymer (Sepinov EMT) could incorporate up to 10% of each alpha hydroxy acid (glycolic acid) individually or up to 20% in conjunction with one another, when combined with the identified low pH, high electrolyte compatible thickeners to create an emulsifier-free cream with a gel cream architecture. Additionally, beta hydroxy acids could be incorporated, specifically salicylic acid, in exemplary and non-limiting embodiments, up to 2% total beta hydroxy acid. Further increasing the uniqueness of this system is the 10% oil phase that is emulsified, yielding an emulsifier-free, low pH gel cream.

Table 2, below, presents the results of the study utilizing 14.4% Glycolic Acid in an emulsion containing 10% oil phase using a series of low pH, high electrolyte compatible thickeners.

TABLE 2

Results of Experiments varying combinations and
amounts of low pH, high electrolyte compatible thickeners
keeping hydroxy acids (glycolic acid) and emollients constant

| RMI | #1 | #4 | #2 | #5 | Total Thickener | Composition Properties |
|---|---|---|---|---|---|---|
| 1 | 0.625 | 4 | 0.625 | 0.25 | 4.875 | Stable Cream |
| 2 | 0.625 | 2 | 1.875 | 0.25 | 4.125 | Stable Cream |
| 3 | 1.25 | 2 | 1.25 | 0 | 3.25 | Stable Cream |
| 4 | 1.875 | 2 | 0.625 | 0.25 | 2.875 | Stable Cream |
| 7 | 1.25 | 2 | 1.25 | 1 | 4.25 | Stable Cream |
| 8 | 1.875 | 2 | 1.875 | 0.75 | 4.625 | Stable Cream |
| 9 | 1.25 | 1 | 1.25 | 0.5 | 2.75 | Stable Cream |
| 10 | 1.25 | 3 | 0 | 0.5 | 3.5 | Stable Cream |
| 12 | 2.5 | 3 | 0.625 | 0.5 | 4.125 | Stable Cream |
| 13 | 1.25 | 4 | 1.25 | 0 | 5.25 | Stable Cream |
| 14 | 1.25 | 3 | 1.25 | 0.5 | 4.75 | Stable Cream |
| 15 | 0.625 | 5 | 0.625 | 0.5 | 6.125 | Stable Cream |
| 16 | 1.875 | 1 | 2.5 | 0 | 3.5 | Stable Cream |
| 18 | 1.875 | 1 | 1.875 | 0.5 | 3.375 | Stable Cream |
| 19 | 1.875 | 2 | 1.25 | 1 | 4.25 | Stable Cream |
| 21 | 2.5 | 3 | 0 | 0.25 | 3.25 | Stable Cream |
| 22 | 0.625 | 3 | 1.25 | 0 | 4.25 | Stable Cream |
| 23 | 0.625 | 3 | 0 | 1 | 4 | Stable Cream |
| 24 | 1.25 | 2 | 1.875 | 1 | 4.875 | Stable Cream |
| 25 | 1.25 | 2 | 1.25 | 0.25 | 3.5 | Stable Cream |
| 28 | 1.875 | 1 | 2.5 | 0.25 | 3.75 | Stable Cream |
| 29 | 1.875 | 1 | 0.625 | 0.5 | 2.125 | Stable Cream |
| 20 | 0.625 | 2 | 0.625 | 1 | 3.625 | Thickening efficacy of #2 is enough to stabilize cream |
| 5 | 0 | 3 | 0.625 | 0.5 | 4.125 | Fluid, lotion-like |
| 6 | 0.625 | 2 | 0.625 | 0.75 | 3.375 | Fluid, lotion-like |
| 17 | 0 | 5 | 0 | 0.75 | 5.75 | Fluid, lotion-like |
| 27 | 0.625 | 3 | 0 | 0.75 | 3.75 | Fluid, lotion-like |
| 11 | 0 | 3 | 1.875 | 0.5 | 5.375 | Separates |
| 26 | 0 | 4 | 1.875 | 0.5 | 6.375 | Separates |
| 30 | 0 | 2 | 1.875 | 0.5 | 4.375 | Separates |

From the data it is evident that Sepinov EMT is significant to producing an emulsifier-free cream containing 10% AHA. In its absence, the resultant composition is hard to emulsify, and forms either a fluid, lotion-like serum or exhibits oil separation overtime. Additionally, even with Sepinov EMT, the data show that it is necessary to have a certain threshold of additional thickeners to acquire a stable cream. For example, Sepinov EMT and AVS alone both provide a liquid serum, whereas a combination of these provides rigidity and structure to form a cream. Referring again to Table 2, three of the thickeners are responsible for the rigidity of the emulsion itself. That is AVS (#2), Sepinov EMT (#1), and Ultrez 30 (#5). The data further show that to obtain a highly desirable level of rigidity in the cream gel architecture, a mixture of all four of AVS (#2), Sepinov EMT (#1), Seipigel (#4) and Ultrez 30 (#5).

Example 3: Inventive Compositions

A suite of inventive compositions were prepared according to the disclosure, each demonstrating a stable gel cream architecture.

TABLE 3

Inventive Compositions with 10% and 20% hydroxy acid (final concentration)

| RAW MATERIAL | INV 1 10% AHA | INV 2 10% AHA | INV 3 10% AHA | INV 4 10% AHA | INV 5 20% AHA |
|---|---|---|---|---|---|
| LACTIC ACID | | | | | 11.11 |
| GLYCOLIC ACID | 14.2 | 14.2 | 14.2 | 14.2 | 14.2 |
| POLYACRYLAMIDE (and) C13-14 ISOPARAFFIN (and) LAURETH-7 | 2 | 2 | 2 | 2 | 2 |
| HYDROXYETHYL ACRYLATE/SODIUM ACRYLOYLDIMETHYL TAURATE COPOLYMER | 1.875 | 1.875 | 1.875 | 1.875 | 1.875 |
| SODIUM ACRYLOYLDIMETHYLTAURATE/ VP CROSSPOLYMER | 1.25 | 1.25 | 1.25 | 1.25 | 1.25 |
| CARBOMER | 1 | 1 | 1 | 1 | 1 |
| ISONONYL ISONONANOATE | 6 | 6 | 6 | 6 | 6 |
| DICAPRYLYL CARBONATE | 3 | 3 | | | |
| SQUALANE | | | 3 | 3 | 3 |
| DIMETHICONE | 0.5 | | | | |
| BEHENYL ALCOHOL | 1 | 1 | 1 | 1 | 1 |
| GLYCERIN | | 10 | | | |
| ADENOSINE | | 0.1 | | | |
| NIACINAMIDE | | 2 | | | |
| PANTHENOL | | 0.5 | | | |
| SODIUM HYDROXIDE | 7.7 | 7.7 | 7.7 | 3.85 | 6.25 |
| WATER | 61.975 | 48.875 | 61.975 | 65.825 | 52.315 |

TABLE 4

| Inventive Compositions with 6% hydroxy acid (final concentration) | | | | | | | |
|---|---|---|---|---|---|---|---|
| RAW MATERIAL | INV 6 6% AHA | INV 7 6% AHA | INV 8 6% AHA | INV 9 6% AHA | INV 10 6% AHA | INV 11 6% AHA | INV 12 6% AHA |
| CAPRYLOYL SALICYLIC ACID | | | | | | 0.3 | |
| GLYCOLIC ACID | 8.57 | 8.57 | 8.57 | 8.57 | 8.57 | 8.57 | 8.57 |
| POLYACRYLAMIDE (and) C13-14 ISOPARAFFIN (and) LAURETH-7 | 2 | 2 | 1.2 | 2 | 2 | | |
| ACRYLAMIDE/SODIUM ACRYLOYLDIMETHYLTAURATE COPOLYMER (and) ISOHEXADECANE (and) POLYSORBATE 80 | | | | | | 2.5 | 2.5 |
| HYDROXYETHYL ACRYLATE/SODIUM ACRYLOYLDIMETHYL ETHYL TAURATE COPOLYMER | 1.875 | 1.875 | 1.5 | 1.5 | 1.5 | 1.5 | 1.875 |
| AMMONIUM ACRYLOYLDIMETHYLTAURATE/VP COPOLYMER | | 1.25 | 0.625 | 0.625 | 0.625 | 0.625 | 0.625 |
| SODIUM ACRYLOYLDIMETHYLTAURATE/VP CROSSPOLYMER | 1.25 | | | | | | |
| CARBOMER | 1 | 1 | 0.8 | 0.8 | 0.8 | 0.8 | 0.8 |
| OCTYLDODECANOL | | | | | | 0.5 | |
| DIISOPROPYL ADIPATE | | | | | | 1.5 | |
| ISONONYL ISONONANOATE | 6 | 6 | 6 | 6 | 6 | 6 | 6 |
| LIMNANTHES ALBA (MEADOWFOAM) SEED OIL | | | | | 3 | | |
| DICAPRYLYL CARBONATE | 3 | | | | | | |
| SQUALANE | | 3 | 3 | 3 | | 3 | 3 |
| BEHENYL ALCOHOL | 1 | 1 | 1 | 1 | 1 | 1 | 1 |
| SODIUM HYDROXIDE | 2.31 | 2.31 | 2.31 | 2.31 | 2.31 | 2.31 | 2.31 |
| WATER | 70.685 | 72.995 | 74.995 | 74.195 | 74.195 | 71.395 | 73.32 |

While the disclosure has been described with reference to a preferred embodiment, it will be understood by those skilled in the art that various changes may be made, and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s).

The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.1% by weight, based on the total weight of the composition.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A cosmetic composition comprising:
    a) a water phase, comprising;
        i. a hydroxy acid system comprising alpha hydroxy acid;
        ii. a primary low pH, high electrolyte compatible thickener comprising Hydroxyethyl Acrylate/Sodium Acrrloyldimethyl Taurate Copolymer;
        iii. at least one secondary low pH, high electrolyte compatible thickener; and
        iv. water, and
    b) an oil phase, comprising:
        i. one or a combination of emollient oils, butters and waxes;
    wherein the composition has a pH in the range from about 1 to about 5.0 and is essentially free of emulsifiers selected from: surfactants with a C10-C20 fatty alcohol or acid hydrophobe condensed with from about 2 to about 100 moles of ethylene oxide or propylene oxide per mole of hydrophobe; C2-C10 alkyl phenols condensed with from 2 to 20 moles of alkylene oxide; mono- and di-fatty acid esters of ethylene glycol; fatty acid monoglyceride; mono- and di-C8-C20 fatty acids; alkyl polyglycosides; saccharide fatty amides; methyl gluconamides; alkyl ether sulfates; ad alkyl ether sulfonates; alkyl sulfates; alkyl sulfonates; alkylbenzene sulfonates; alkyl sulfosuccinates; dialkyl sulfosuccinates; C8-C20 acyl isethionates; C8-C20 alkyl ether phosphates; alkylethercarboxylate; and combinations of these, and wherein the composition comprises a gel cream architecture.

2. The cosmetic composition according to claim 1, the hydroxy acid system comprising a combination of hydroxy acids selected from two or more alpha hydroxy acids, at least one alpha hydroxy acid and at least one beta hydroxy acid, and two or more alpha hydroxy acids and at least one beta hydroxy acid.

3. The cosmetic composition according to claim 1, the hydroxy acid system comprising at least one of glycolic acid, lactic acid and citric acid.

4. The cosmetic composition according to claim 1, the at least one secondary thickener comprising one or more of Sodium Acryloyldimethyltaurate/VP Crosspolymer, Sodium Acryloyldimethyltaurate/VP Copolymer, Polyacrylamide (and) C13-14 Isoparaffin (and) Laureth-7, Carbomer, Acrylamide/Sodium Acryloyldimethyltaurate Copolymer (and) Isohexadecane (and) Polysorbate 80.

5. The cosmetic composition according to claim 1, the at least one secondary thickener comprising (a) one or both of Sodium Acryloyldimethyltaurate/VP Crosspolymer and Carbomer, and (b) one of Polyacrylamide (and) C13-14 Isoparaffin (and) Laureth-7 and Acrylamide/Sodium Acryloyldimethyltaurate Copolymer (and) Isohexadecane (and) Polysorbate 80.

6. The cosmetic composition according to claim 1, the one or a combination of emollients comprising one or more of a fatty alcohol, a fatty acid ester, a alkyl glucoside, a silicone oil, and combinations of these.

7. The cosmetic composition according to claim 1, the one or a combination of emollients comprising octyldodecanol, diisopropyl adipate, isononyl isononanoate, limnanthes alba (meadowfoam) seed oil, dicaprylyl carbonate, squalane, dimethicone, Cetearyl Alcohol and Cetearyl Glucoside, and behenyl alcohol, and combinations of these.

8. The cosmetic composition according to claim 1, wherein the hydroxy acid system is present from about 6% to more than about 20% by weight based on the weight of the composition.

9. The cosmetic composition according to claim 1, wherein the primary thickener is present from about 0.5% to about 5% by weight based on the weight of the composition.

10. The cosmetic composition according to claim 1, wherein each of the at least one secondary thickener is present from about 0.5% to about 8% by weight based on the weight of the composition.

11. The cosmetic composition according to claim 1, wherein water is present from about 55% to about 80% by weight based on the weight of the composition.

12. The cosmetic composition according to claim 1, wherein the composition is essentially free or devoid of emulsifiers selected from the group consisting of: sorbitan; polyoxyethylene sorbitan; PEG-100 Stearate; PEG-20 Stearate; Sucrose Stearate; Glyceryl Stearate; Disodium Ethylene Dicocamide PEG-15 Disulfate; Sodium Steroyl Glutamate; Steareth-100; Acrylates/C10-30 Alkyl Acrylate Crosspolymer; and combinations of these.

13. A cosmetic composition comprising:
a) a water phase, comprising;
    i. a hydroxy acid system comprising a combination of hydroxy acids selected from two or more alpha hydroxy acids, at least one alpha hydroxy acid and at least one beta hydroxy acid, and two or more alpha hydroxy acids and at least one beta hydroxy acid;
    ii. a primary low pH, high electrolyte compatible thickener comprising Hydroxyethyl Acrylate/Sodium Acrrloyldimethyl Taurate Copolymer;
    iii. at least one secondary low pH, high electrolyte compatible thickener comprising one or more of Sodium Acryloyldimethyltaurate/VP Crosspolymer, Sodium Acryloyldimethyltaurate/VP Copolymer, Polyacrylamide (and) C13-14 Isoparaffin (and) Laureth-7, Carbomer, Acrylamide/Sodium Acryloyldimethyltaurate Copolymer (and) Isohexadecane (and) Polysorbate 80; and
    iv. water, and
b) an oil phase, comprising:
    i. one or a combination of emollient oils comprising one or more of a fatty alcohol, a fatty acid ester, a alkyl glucoside, a silicone oil, and combinations of these;
    wherein the composition has a pH in the range from about 1 to about 5.0 and is essentially free of emulsifiers selected from: surfactants with a C10-C20 fatty alcohol or acid hydrophobe condensed with from about 2 to about 100 moles of ethylene oxide or propylene oxide per mole of hydrophobe; C2-C10 alkyl phenols condensed with from 2 to 20 moles of alkylene oxide; mono- and di-fatty acid esters of ethylene glycol; fatty acid monoglyceride; mono- and di-C8-C20 fatty acids; alkyl polyglycosides; saccharide fatty amides; methyl gluconamides; alkyl ether sulfates; ad alkyl ether sulfonates; alkyl sulfates; alkyl sulfonates; alkylbenzene sulfonates; alkyl sulfosuccinates; dialkyl sulfosuccinates; C8-C20 acyl isethionates; C8-C20 alkyl ether phosphates; alkylethercarboxylate; and combinations of these, and wherein the composition comprises a gel cream architecture.

14. The cosmetic composition according to claim 13, wherein the composition is essentially free or devoid of emulsifiers selected from the group consisting of: sorbitan; polyoxyethylene sorbitan; PEG-100 Stearate; PEG-20 Stearate; Sucrose Stearate; Glyceryl Stearate; Disodium Ethylene Dicocamide PEG-15 Disulfate; Sodium Steroyl Glutamate; Steareth-100; Acrylates/C10-30 Alkyl Acrylate Crosspolymer; and combinations of these.

15. A cosmetic composition comprising:
a) a water phase, comprising the following, each present by weight based on the weight of the composition;
    i. a hydroxy acid system comprising alpha hydroxy acid present from about 6% to more than about 20%;
    ii. a primary low pH, high electrolyte compatible thickener comprising Hydroxyethyl Acrylate/Sodium Acrrloyldimethyl Taurate Copolymer present from about 0.5% to about 5%;
    iii. at least one secondary low pH, high electrolyte compatible thickener, each of the at least one secondary thickener present from about 0.5% to about 8%; and
    iv. water present from about 55% to about 80% by weight based on the weight of the composition, and
b) an oil phase, comprising:
    i. one or a combination of emollient oils;
    wherein the composition has a pH in the range from about 1 to about 5.0 and is essentially free of emulsifiers selected from: surfactants with a C10-C20 fatty alcohol or acid hydrophobe condensed with from about 2 to about 100 moles of ethylene oxide or propylene oxide per mole of hydrophobe; C2-C10 alkyl phenols condensed with from 2 to 20 moles of alkylene oxide; mono- and di-fatty acid esters of ethylene glycol; fatty acid monoglyceride; mono- and di-C8-C20 fatty acids; alkyl polyglycosides; saccharide fatty amides; methyl gluconamides; alkyl ether sulfates; ad alkyl ether sulfonates; alkyl sulfates; alkyl sulfonates; alkylbenzene sulfonates; alkyl sulfosuccinates; dialkyl sulfosuccinates; C8-C20 acyl isethionates; C8-C20 alkyl ether phosphates; alkylethercarboxylate; and combinations of these, and wherein the composition comprises a gel cream architecture.

16. The cosmetic composition according to claim 15, wherein the composition is essentially free or devoid of emulsifiers selected from: surfactants with a C10-C20 fatty alcohol or acid hydrophobe condensed with from about 2 to about 100 moles of ethylene oxide or propylene oxide per mole of hydrophobe; C2-C10 alkyl phenols condensed with from 2 to 20 moles of alkylene oxide; mono- and di-fatty acid esters of ethylene glycol and combinations of these.

17. The cosmetic composition according to claim 15, wherein the primary low pH, high electrolyte compatible thickener is present from about 0.625% to about 2.5%, and wherein each of the at least one secondary low pH, high electrolyte compatible thickener is present from about 0.5% to about 2%, each present by weight based on the total weight of the composition.

18. The cosmetic composition according to claim 15, wherein the one or a combination of emollient oils is present from about 5% to more than about 20% by weight based on the weight of the composition.

19. The cosmetic composition according to claim 15, wherein the composition is essentially free or devoid of emulsifiers selected from: surfactants with a C10-C20 fatty alcohol or acid hydrophobe condensed with from about 2 to about 100 moles of ethylene oxide or propylene oxide per mole of hydrophobe; C2-C10 alkyl phenols condensed with from 2 to 20 moles of alkylene oxide; mono- and di-fatty acid esters of ethylene glycol and combinations of these.

20. The cosmetic composition according to claim 15, wherein the composition is essentially free or devoid of emulsifiers selected from the group consisting of: sorbitan; polyoxyethylene sorbitan; PEG-100 Stearate; PEG-20 Stearate; Sucrose Stearate; Glyceryl Stearate; Disodium Ethylene Dicocamide PEG-15 Disulfate; Sodium Steroyl Glutamate; Steareth-100; Acrylates/C10-30 Alkyl Acrylate Crosspolymer; and combinations of these.

* * * * *